(12) United States Patent
Wisselink

(10) Patent No.: US 10,646,363 B2
(45) Date of Patent: May 12, 2020

(54) ENDOVASCULAR DEVICE DELIVERY SYSTEM

(75) Inventor: Willem Wisselink, Bussum (NL)

(73) Assignee: Cook Medical Technologies LLC, Bloomington, IN (US)

( * ) Notice: Subject to any disclaimer, the term of this patent is extended or adjusted under 35 U.S.C. 154(b) by 900 days.

(21) Appl. No.: 12/342,996

(22) Filed: Dec. 23, 2008

(65) Prior Publication Data

US 2009/0171429 A1 Jul. 2, 2009

Related U.S. Application Data

(63) Continuation of application No. 12/341,679, filed on Dec. 22, 2008, now abandoned.

(60) Provisional application No. 61/017,023, filed on Dec. 27, 2007.

(51) Int. Cl.
  *A61F 2/06* (2013.01)
  *A61F 2/95* (2013.01)
  *A61F 2/07* (2013.01)

(52) U.S. Cl.
  CPC .................. *A61F 2/95* (2013.01); *A61F 2/07* (2013.01); *A61F 2002/067* (2013.01); *A61F 2250/006* (2013.01); *A61F 2250/0098* (2013.01)

(58) Field of Classification Search
  CPC .................. A61F 2/95; A61F 2002/067; A61F 2250/0098; A61F 2250/006; A61F 2/07
  See application file for complete search history.

(56) References Cited

U.S. PATENT DOCUMENTS

| 2,947,415 | A | * | 8/1960 | Garth | ............................ 206/364 |
| 5,171,233 | A | | 12/1992 | Amplatz et al. | |
| 5,571,172 | A | | 11/1996 | Chin | |
| 6,045,557 | A | | 4/2000 | White et al. | |
| 6,099,558 | A | * | 8/2000 | White et al. | ................. 623/1.16 |
| 6,302,905 | B1 | | 10/2001 | Goldsteen et al. | |
| 6,478,813 | B1 | | 11/2002 | Keith et al. | |
| 6,517,550 | B1 | * | 2/2003 | Konya et al. | ................. 606/113 |

(Continued)

FOREIGN PATENT DOCUMENTS

| JP | 2002-526176 | 8/2002 |
| JP | 2003-521328 | 7/2003 |

(Continued)

OTHER PUBLICATIONS

PCT International Search Report/Written Opinion of the International Searching Authority (the European Patent Office) regarding Application No. PCT/US2008/014046, dated May 8, 2009, 18 pages.

(Continued)

*Primary Examiner* — Amy R Weisberg
(74) *Attorney, Agent, or Firm* — Brinks Gilson & Lione

(57) ABSTRACT

An endovascular delivery system includes a bifurcated prosthesis disposed on a delivery device and a snare catheter having a snare opening system. A sheath is slidably disposed over at least a portion of the prosthesis and at least a portion of the snare catheter. One end of the snare catheter resides external to the prosthesis in the delivery system and the other end at least partially resides in a limb of the prosthesis. A snare mechanism is disposed within the snare catheter that is capable of forming a loop external to the snare catheter through the opening and snaring a guidewire for placement in a limb of the prosthesis.

24 Claims, 17 Drawing Sheets

(56) References Cited

U.S. PATENT DOCUMENTS

| | | | |
|---|---|---|---|
| 6,537,284 B1 | 3/2003 | Inoue | |
| 6,554,842 B2 | 4/2003 | Heuser et al. | |
| 6,641,606 B2* | 11/2003 | Ouriel et al. | 623/1.12 |
| 6,660,030 B2 | 12/2003 | Shaolian et al. | |
| 6,666,880 B1* | 12/2003 | Chiu | A61F 2/958 606/194 |
| 6,761,733 B2 | 7/2004 | Chobotov et al. | |
| 6,808,534 B1 | 10/2004 | Escano | |
| 6,916,335 B2 | 7/2005 | Kanji | |
| 7,235,083 B1* | 6/2007 | Perez et al. | 606/108 |
| 2001/0049534 A1 | 12/2001 | Lachat | |
| 2002/0123698 A1 | 9/2002 | Garibotto et al. | |
| 2004/0243221 A1* | 12/2004 | Fawzi et al. | 623/1.23 |
| 2005/0182476 A1* | 8/2005 | Hartley et al. | 623/1.11 |
| 2005/0228476 A1* | 10/2005 | Dimatteo et al. | 623/1.11 |
| 2007/0219614 A1 | 9/2007 | Hartley | |
| 2008/0208309 A1* | 8/2008 | Saeed | 623/1.11 |

FOREIGN PATENT DOCUMENTS

| | | |
|---|---|---|
| WO | WO 0020064 | 4/2000 |
| WO | WO 0156484 | 8/2001 |
| WO | WO 2008/103463 A2 | 8/2008 |
| WO | WO 2008/103463 | 10/2012 |

OTHER PUBLICATIONS

PCT Notification of Transmittal of the International Preliminary Report on Patentability regarding Application No. PCT/US2008/014046, dated Dec. 4, 2009, 8 pages.

Patent Examination Report No. 1 for corresponding AU patent application No. 2008343765, dated Oct. 19, 2012, 3 pages.

Notice of Grounds for Rejection for corresponding JP patent application No. 2010-540666 translation and original document, dated Feb. 26, 2013, 5 pages.

\* cited by examiner

ENDOVASCULAR DEVICE DELIVERY SYSTEM

This application claims the benefit of priority from U.S. Provisional Application No. 61/017,023, filed Dec. 27, 2007, and is a continuation of U.S. application Ser. No. 12/341,679, filed Dec. 22, 2008, which are incorporated by reference.

BACKGROUND

This invention relates to delivery systems for implanting endoluminal devices within the human or animal body for treatment of endovascular disease. In particular, this invention relates to delivery systems having a novel catheter system to cannulate a contralateral portion of an endoluminal device.

The functional vessels of human and animal bodies, such as blood vessels and ducts, occasionally weaken or even rupture. For example, the aortic wall can weaken, resulting in an aneurysm. One surgical intervention for weakened, aneurismal, or ruptured vessels involves the use of stent grafts to replace or repair the vessel. Stent grafts may be formed from a tube of a biocompatible material in combination with one or more stents to maintain a lumen therethrough. The stents are attached to the graft material in a number of ways, including by suturing the stent to the graft material, embedding the stent in the graft material, adhesively attaching the stent to the material and the like.

The above-described examples are only some of the applications in which endoluminal devices are used by physicians. Many other applications for endoluminal devices are known and/or will be developed in the future. For example, in addition to the use of stents and stent-grafts to treat vascular stenoses and aneurysms, similar procedures also may be used to deploy vascular filters, occluders, artificial valves and other endoprosthetic device.

A prosthesis of this type can, for example, treat aneurysms of the abdominal aortic, iliac, or branch vessels such as the renal arteries. Hence, an endoluminal prosthesis can be of a unitary construction or be comprised of multiple prosthetic modules. A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system also may accommodate deployment by allowing the proper placement of one module before the deployment of an adjoining module.

Modular systems are typically assembled in situ by overlapping the tubular ends of the prosthetic modules so that the end of one module sits partially inside the other module, preferably forming circumferential apposition through the overlap region. This attachment process is sometimes referred to as "tromboning." The connections between prosthetic modules are typically maintained by the friction forces at the overlap region and enhanced by the radial force exerted by the internal prosthetic module on the external prosthetic modules where the two overlap. The fit may be further enhanced by stents fixed to the modules at the overlap region or other treatment of the graft material at the connection points.

For example, in the treatment of an abdominal aortic aneurysm, a bifurcated device including a main body and two limbs may be deployed within the aneurysm. Further extension of one or more of the limbs into their corresponding iliac arteries may be desired for full repair of the aneurysm. With some bifurcated devices, one of the limbs may extend into a corresponding iliac artery, while the other limb, for example a shorter limb (referred to here as the contralateral limb) does not.

In this case, the shorter limb may remain in the body of the aneurysm above the opening of its respective iliac artery. In order to extend this limb into its respective iliac artery one or more extensions may be used in an overlapping manner, as described above, to extend the shorter limb into the iliac artery.

Normally, extension of the contralateral limb is accomplished by inserting a guide wire through the femoral artery associated with the iliac artery in which leg extensions are to be inserted and overlapped with the contralateral limb of the body. The wire is inserted into the femoral artery, up through the iliac artery, into the aneurysmal space and then, desirably, is manipulated to be inserted into the contralateral limb of the main prosthesis.

A prosthetic module then is advanced up the guide wire, and partially inserted into the contralateral limb of the bifurcated prosthesis in an overlapping manner. The module is then expanded to contact the limb and seal against the limb. This procedure can be performed to attach several sequential modules as needed to extend the contralateral limb. Similar extension may be performed on the other limb if needed.

This insertion process, though effective, difficulties may arise in the cannulation of the shorter limb, particularly in cases where the vascularity is tortuous, a common issue; where the graft is short bodied, thus increasing the distance between the femoral artery access site and the prosthesis target site; or when the shorter limb is located within the aneurysm, thus presenting a large space in which the guidewire must navigate to reach the shorter limb. In addition, blood continues to flow through the vessel, which may further contribute to movement of the wire during placement.

Thus, this procedure requires both high precision and accuracy on the part of the physician performing the procedure as the aneurysmal sac may be large. Timing also is an important factor. Proper wire placement in this situation may take multiple attempts and, in some cases, be impossible. Hence, placement of the wire may be time consuming and unpredictable. With patients suffering from aneurysms, time is a critical factor, as an aneurysm may rupture at any time.

BRIEF SUMMARY

The present invention relates to delivery systems for implanting endoluminal devices within the human or animal body for treatment of endovascular disease. In particular, this invention relates to a novel delivery system to effectively cannulate a contralateral limb of an endoluminal device for the placement of additional prosthetic modules in a quick and precise manner.

The endovascular delivery device includes at least a delivery device having a prosthetic device mounted on the device and a sheath at least partially over the prosthetic device. Further included in the delivery device is a snare catheter including a snare mechanism disposed within the snare catheter. The snare catheter is provided with a snare opening system in between the proximal and distal end of the catheter. The snare mechanism may form a loop external to the snare catheter and may have at least one free end at the distal end of the device.

Using imaging techniques, such as fluoroscopy, the main delivery system, including the prosthesis to be placed and the snare catheter is delivered to the target site. The method may include inserting a guide wire into the patient, maneuvering the guide wire to a location in a vessel, advancing the delivery device over the guide wire, and deploying the main stent graft at a site of repair. In the case of a bifurcated prosthesis, the device may include a main body and an ipsilateral limb and a contralateral limb extending from the main body. Once the main body has been placed at the target location, a guidewire is advanced through the other femoral artery into the aorta at a point below the opening of the contralateral limb.

The catheter may then be advanced to a position within the contralateral limb portion of the main stent graft such that the catheter opening is distal to the contralateral limb portion. The snare mechanism may be manipulated to form a loop through the snare opening. A contralateral guide wire may be inserted through a contralateral vessel and captured by the snare mechanism loop. The free ends of the snare mechanism may be manipulated to tighten the loop to pull the captured guidewire up against the body of the snare catheter. The snare catheter may then be advanced further into the main body so that the guide wire is maneuvered into the contralateral limb. A contralateral limb stent graft may then be advanced over the contralateral guide wire and docked into place in the contralateral limb of the main body.

This invention reduces the time and difficulty of positioning a contralateral stent graft into the shorter contralateral limb portion of the main prosthesis. The snare mechanism provides a means for capturing a contralateral guidewire and subsequently inserting the contralateral guide wire into the contralateral limb portion of the main prosthesis, eliminating the need to directly maneuver the contralateral guide wire into the contralateral limb portion.

These and other features, aspects, and advantages will become better understood with regard to the following detailed description, appended claims and accompanying drawings.

DETAILED DESCRIPTION OF THE DRAWINGS AND THE PREFERRED EMBODIMENTS

Figure 1:
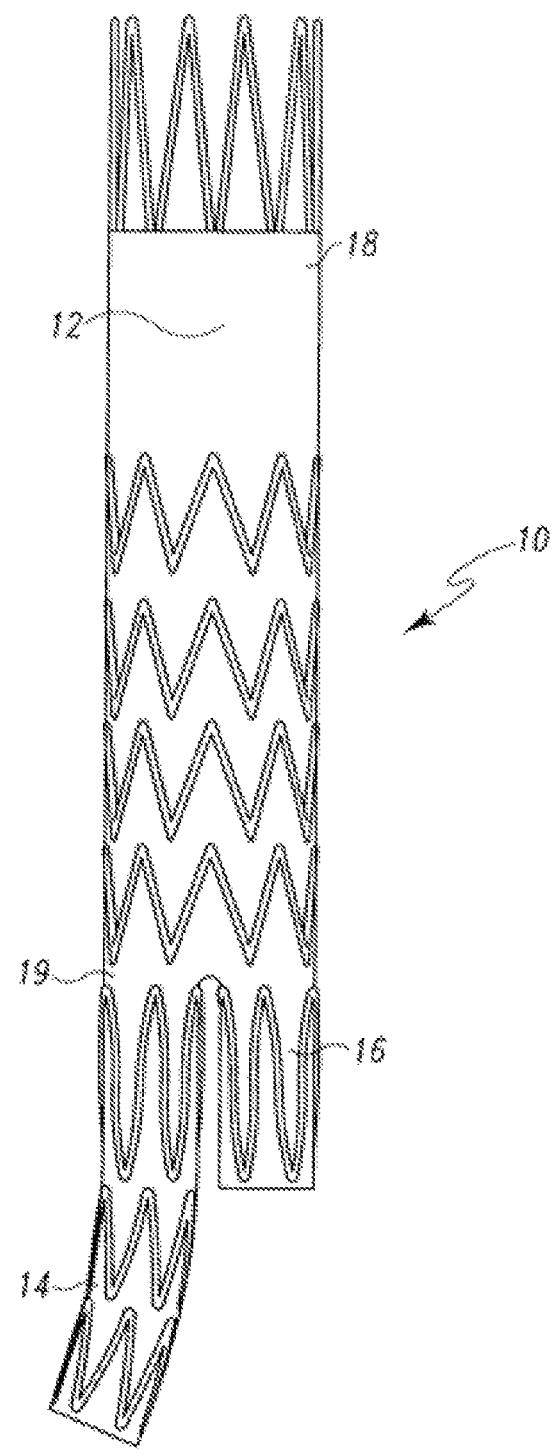
FIG. 1 shows a bifurcated endoluminal prosthesis.

Unless defined otherwise, all technical and scientific terms used herein have the same meaning as commonly understood to one of ordinary skill in the art to which this invention belongs.

Throughout this specification and in the appended claims, the terms "distal" and "distally" are intended to refer to a location or direction that is, or a portion of a device that when implanted, or placed within the blood vessel is further downstream in the direction of or with respect to blood flow. The terms "proximal" and "proximally" refer to a location or direction that is, or a portion of a device that when implanted, or placed within the blood vessel, is further upstream in the direction of or with respect to blood flow.

The terms "ipsilateral" and "contralateral" typically refer to opposing portions of a corporeal lumen having symmetric right and left sides. "Ipsilateral" refers to those portions residing on the same side through which the grafting system enters the corporeal lumen, while "contralateral" refers to the opposite portions. Therefore, this distinction is dependent on whichever side (right or left) the physician decides to insert the grafting system. The portions of the grafting system which reside or operate within the symmetric vessels of the corporeal lumen use the same terminology. Here, when referring to the Figures, the ipsilateral limb is shown on the left and the contralateral limb is shown on the right.

The term "prosthesis" means any replacement for a body part or function of that body part. It can also mean a device that enhances or adds functionality to a physiological system.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be coated with a polymeric material, for example, by immersion in molten polymer or any other method known to one of skill in the art. The stent may be located on the exterior of the device, the interior of the device, or both. A stent may be self-expanding, balloon-expandable or may have characteristics of both. A variety of other stent configurations are also contemplated by the use of the term "stent."

The term "graft or graft material" describes an object, device, or structure that is joined to or that is capable of being joined to a body part to enhance, repair, or replace a portion or a function of that body part. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto the mandrel of the present invention. Preferably, polymers of the present invention, although added in layers onto the mandrel, after curing, result in one layer that encapsulates a stent or woven graft. This also aids in decreasing the incidence of delamination of the resulting endovascular prosthesis. A stent may be attached to a graft to form a "stent graft."

The terms "patient," "subject," and "recipient" as used in this application refer to any mammal, especially humans.

The present invention relates to delivery systems for implanting endoluminal devices within the human or animal body for treatment of endovascular disease. In particular, this invention relates to a novel delivery system to effectively cannulate a contralateral limb of an endoluminal device for the placement of additional prosthetic modules in a quick and precise manner.

FIG. 1 shows a bifurcated endovascular prosthesis 10. Prosthesis 10 has a main body 12, and two limbs, an ipsilateral limb 14, a contralateral limb 16, a proximal end 18 and a distal end 19. As used here, in a bifurcated system having two limbs, where one limb is longer than the other, the ipsilateral limb 14 refers to the longer limb and the contralateral limb 16 refers to the shorter limb.

Figure 2:
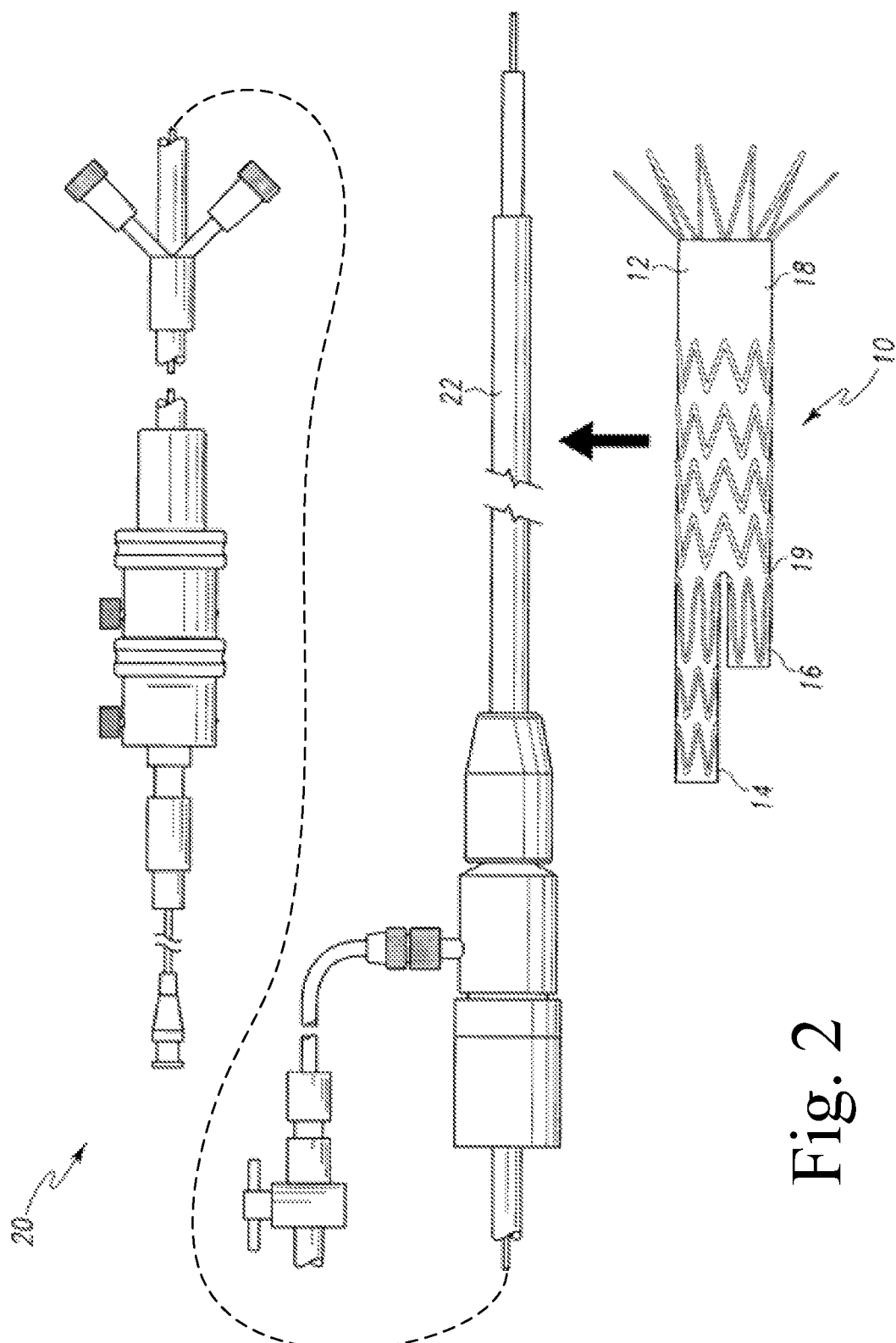
FIG. 2 shows an exemplary delivery system for a bifurcated prosthesis.
Figure 3:
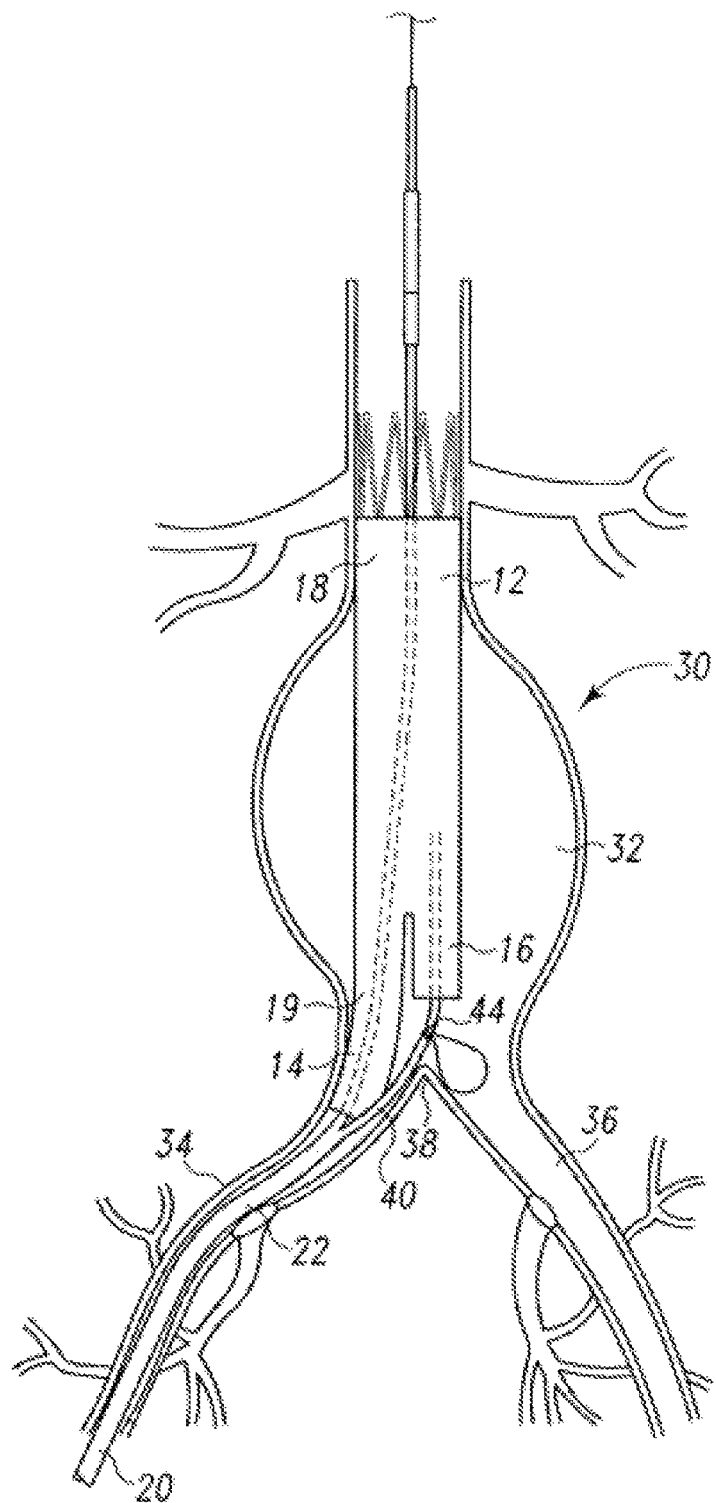
FIG. 3 shows an exemplary delivery system for a bifurcated prosthesis and a guidewire snare mechanism.

FIG. 2 shows an example of a type of delivery device 20 used to deploy the prosthesis 10 of FIG. 1. The prosthesis 10 is mounted on the delivery system 20 in the area indicated by the arrow, and enclosed in sheath 22. FIG. 3 shows a deployed prosthesis 10 in a body vessel 30, having an aneurysm 32, an ipsilateral iliac artery 34, a contralateral iliac artery 36, and a bifurcation 38, where the two iliac arteries branch.

Generally the prosthesis 10 is loaded on to the delivery device 20 in the area indicated by the arrow. The prosthesis is maintained in a compressed delivery state until deployment by sheath 22. In the case of repairing an abdominal aortic aneurysm, for example, the delivery device 20, often referred to as an introducer, is introduced into a patient via an incision in one of the patient's femoral arteries. The introducer is then advanced through the patient's femoral artery into the respective iliac artery and to the aneurysm site. Under fluoroscopy or other imaging techniques, the physician monitors the advancement of the introducer to ensure proper placement. Radiopaque or other imagable markers and the like may be placed at various points on the introducer and/or the prosthesis to aid in visualization.

FIG. 3 shows the prosthesis of FIGS. 1 and 2 deployed in an abdominal aortic aneurysm. As shown, in FIG. 3, the main body 12 has been deployed from the delivery system by withdrawal of sheath 22, and is positioned in the vessel 30 and anchored to the vessel 30 at the proximal end 18. The ipsilateral limb 14 has been deployed in the ipsilateral iliac artery 34. The contralateral limb 16, as shown, is positioned about its respective artery and is located in the aneurysmal sac 32.

In accordance with the present invention, the novel delivery system described here, as shown in FIG. 3, further includes at least a snare catheter 40 including a snare mechanism 42 (not shown in FIG. 3) disposed within the snare catheter 40. The snare catheter 40 is provided in the delivery system 20 with the prosthesis 10. The snare catheter 40 is provided with a snare opening system 44 in the side of the snare catheter 40. The snare opening system 44 may include at least one hole in the side wall of the snare catheter 40 to accommodate the snare mechanism 42. Prior to retraction of sheath 22, the snare catheter 40 is disposed at least partially within the sheath 22.

At least a portion of the snare catheter 40 lies within the sheath 22 in a position adjacent to and external of the ipsilateral limb 14. Another portion of the snare catheter 40 lies within the contralateral limb 16 of the prosthesis 10. As shown in FIG. 3, after the prosthesis 10 has been deployed, a portion of the snare catheter 40 runs along side and external to the ipsilateral limb 14 and a portion of the snare catheter 40 is disposed in the contralateral limb 16 and may extend into the lumen of the main body 12. The snare opening system 44, at this point, remains outside of the contralateral limb 16 within the aneurysmal sac as shown. Radiopaque markers (not shown) may be provided at or near the opening 44 so as to facilitate proper placement during introduction.

As set forth above, the snare catheter 40 includes a snare opening system 44 in the side wall of the snare catheter 40 to permit a guide wire capture or snare mechanism 42 to exit the snare opening system 44 and capture a guidewire or other device. For the purposes of this application, snare mechanism means any type of capture device that is capable of snaring or grasping another device, such as a guide wire.

Figure 4:
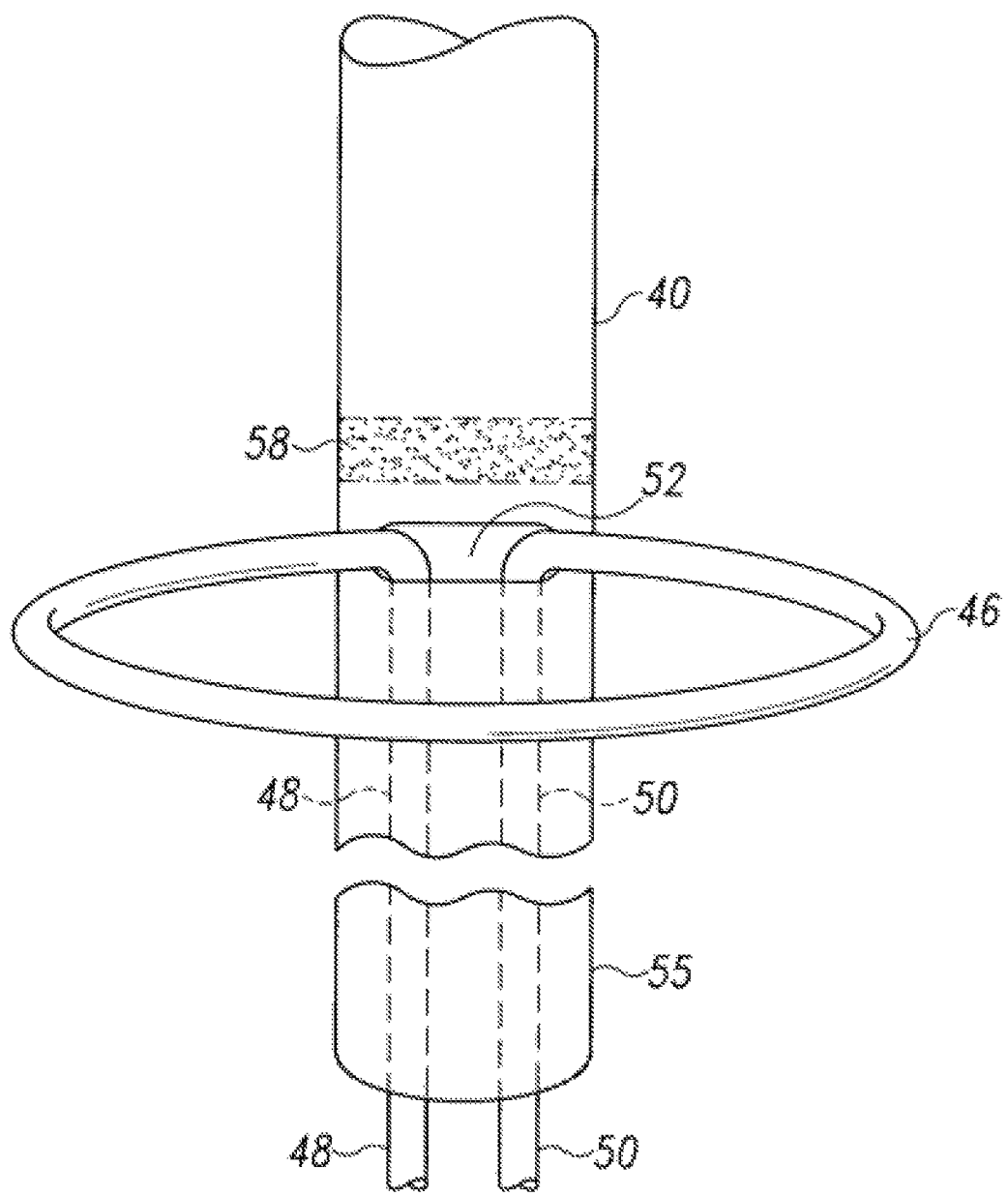
FIG. 4 is a partial view of a snare catheter having a one hole opening system.
Figure 5:
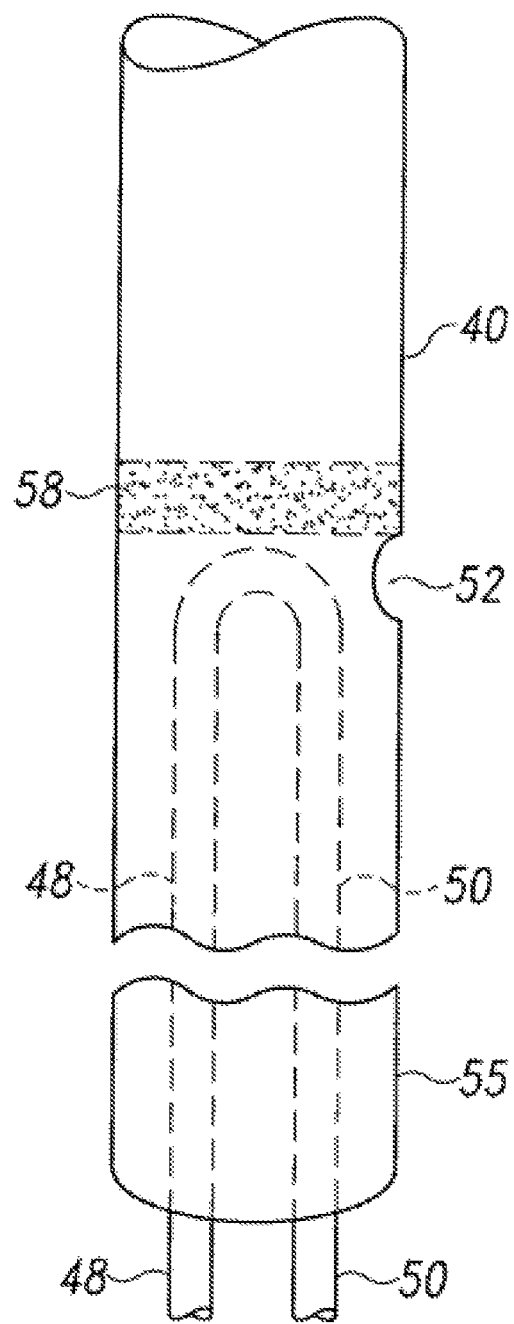
FIG. 5 is another partial view of the snare catheter of FIG. 4.

The snare mechanism 42 may comprise a wire, or bundle of two or more wires, that is formed into at least one loop 46. The loop 46 may be disposed inside the snare catheter 40 until deployment. FIG. 4 shows a snare catheter 40 where the snare opening system 44 comprises a single hole 52. As shown in FIG. 5, the wire that forms the snare mechanism 42 is a single wire that has been looped within the snare catheter 40. Ends 48 and 50 of the wire of the snare mechanism 42 extend through the snare catheter 40, and at least one extends out of the distal end 55 of the snare catheter 40 and out of the delivery system (not shown) and out of the patient's body (not shown) so as to permit manipulation of the snare loop 46 by the physician.

Both ends 48 and 50 of the snare mechanism may exit the delivery system and the body of the patient so that one or both ends may be used by the physician performing the procedure to manipulate the snare loop 46. Alternatively, one end may be attached to snare catheter 40, while the other end remains free. In this example, the free end provides for the manipulation of the snare mechanism 42. In another example, both ends may be joined together by any known means.

As set forth above, the snare opening system 44 may include one or more holes to accommodate the snare mechanism 42. The single hole 52 opening system is shown in FIGS. 4 and 5. In this example, the snare mechanism 42 is formed into a loop within the snare catheter 40. A stopping mechanism 58, located at or just above the hole 52 acts as a stop mechanism to prevent the snare mechanism from moving further down the snare catheter 40 and to encourage the loop to exit from the hole 52 when the snare mechanism is manipulated by the operator. As shown in FIG. 4, by applying pressure to the wires of the snare mechanism, the loop 46 may exit from the hole 52 to form an external snare as shown in FIG. 6.

Figure 6:
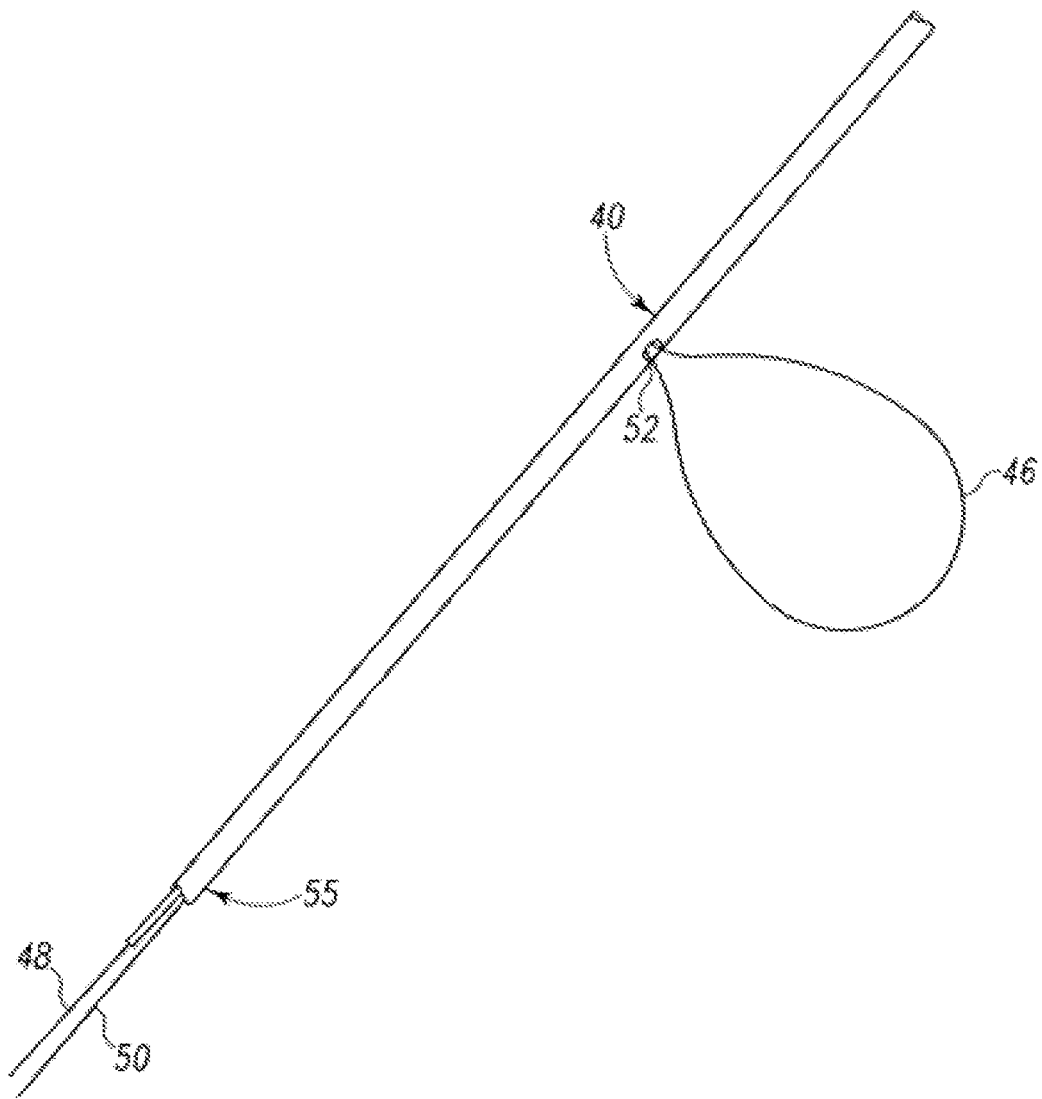
FIG. 6 is a perspective partial view of the snare catheter of FIGS. 4 and 5 with the snare mechanism extending from the opening system.

As shown in FIG. 6, loop 46 exits from hole 52 to form a snaring device. The ends 48, 50 of the wire forming loop 46 extend through the length of the catheter 40 and out of the distal end 55 of the snare catheter 40. Although a single round or ovular loop is shown, other shapes are contemplated.

Figure 7:
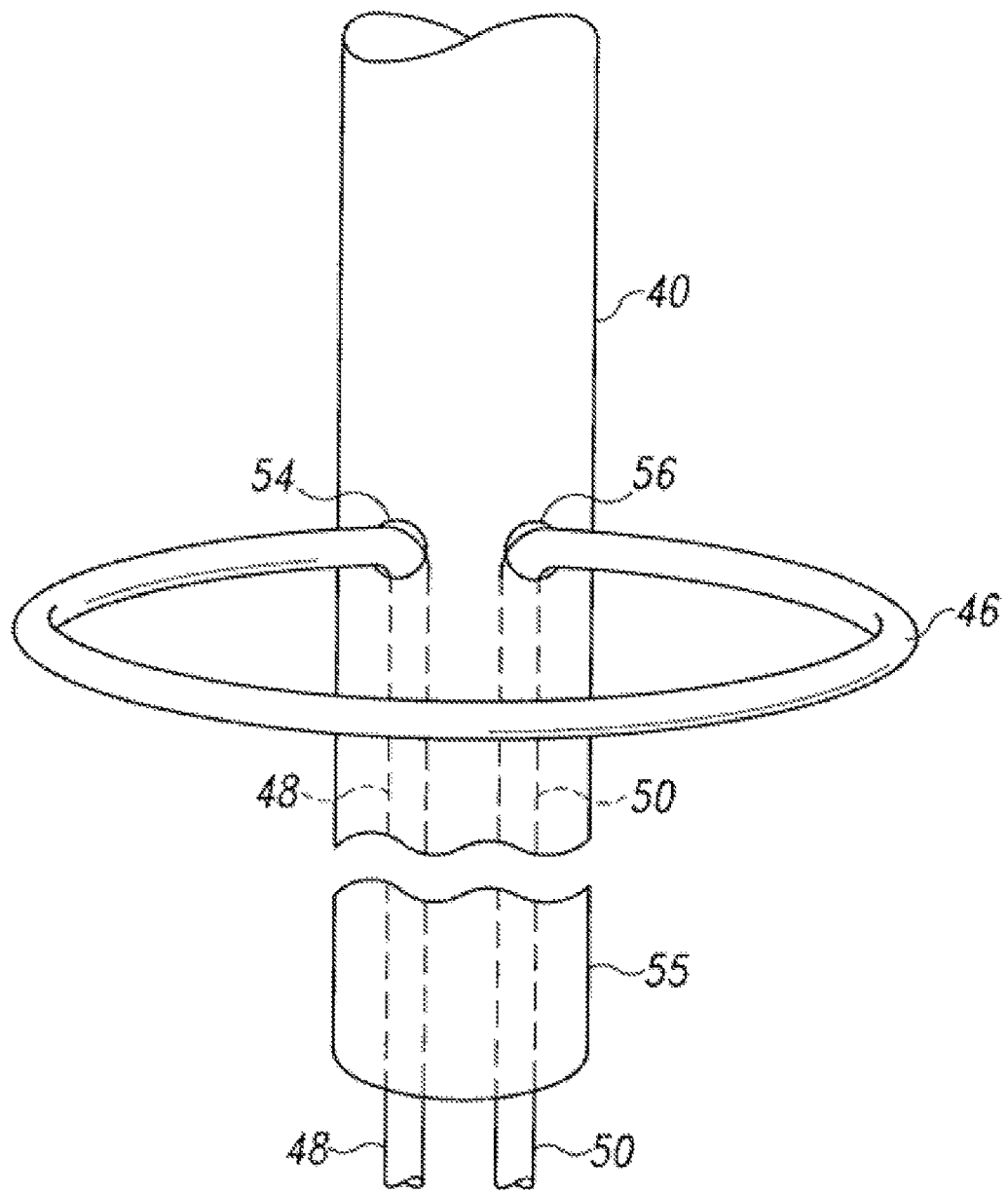
FIG. 7 is a partial view of a snare catheter having a two hole opening system.
Figure 8:
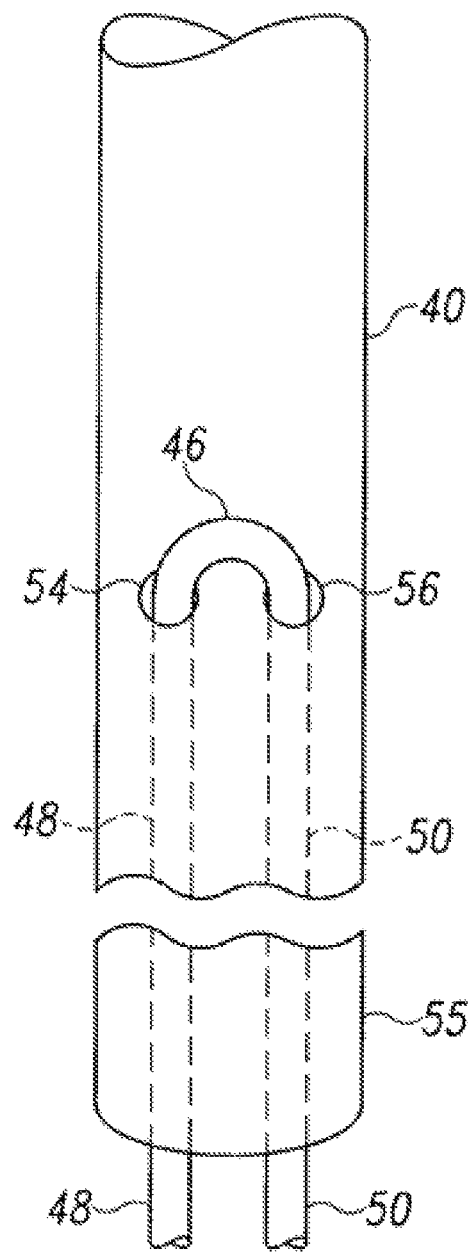
FIG. 8 is another partial view of the snare catheter of FIG. 7.

FIG. 7 shows a double hole 54, 56 opening system. In this example, the snare catheter 40 has at least two holes 54, 56. The holes may be placed roughly side by side or may be up to 180 degrees apart from one another on the circumference of the snare catheter 40. In this example, one end of the snare mechanism 42 exits from the lumen of the snare catheter 40 out of one of the holes and reenters the snare lumen through the other hole to form loop 46. As shown in FIG. 8, during delivery, the ends 48, 50 of the snare mechanism may be pulled to hold the loop 46 taut against the snare exterior so as to reduce the profile of the snare mechanism 42 and avoid entangling other items. This pulling taut also provides the ability to pull a snared device snugly against the snare catheter 40 for manipulation.

Figure 9:
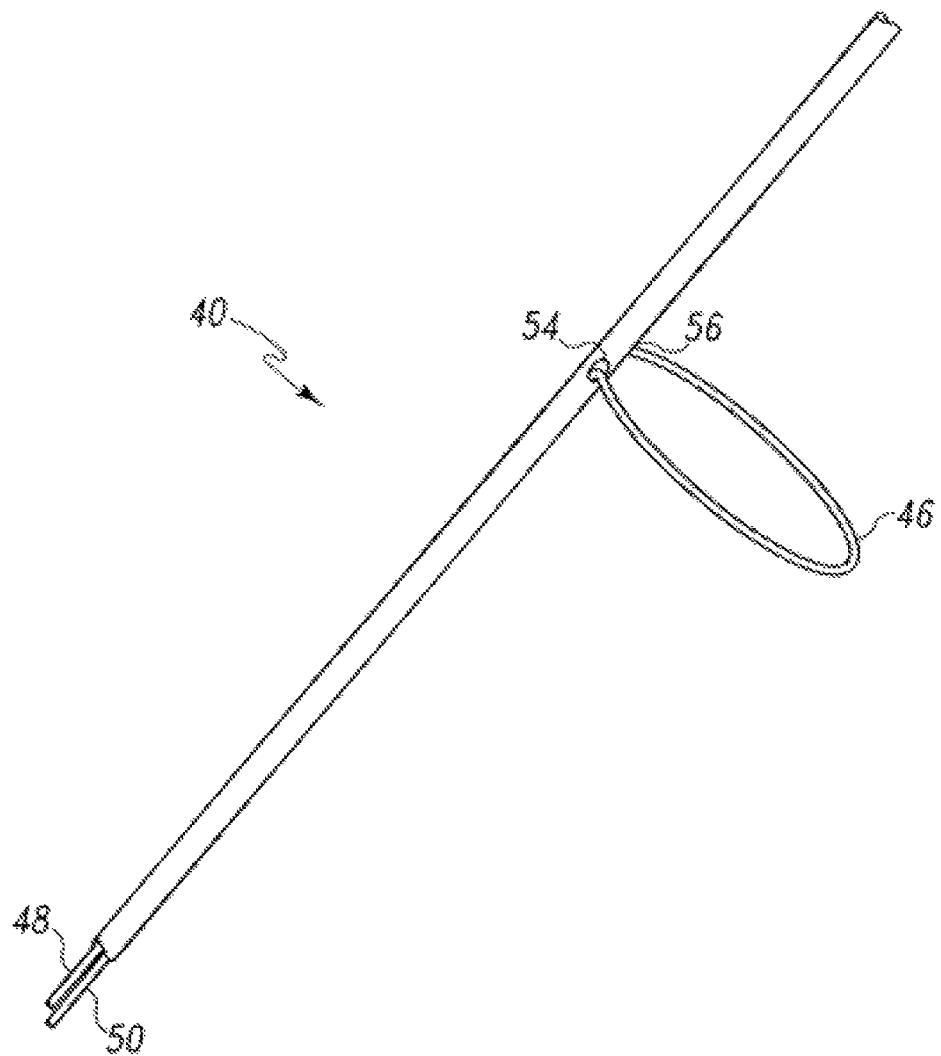
FIG. 9 is a perspective partial view of the snare catheter of FIGS. 7 and 8 with the snare mechanism extending from the opening system.
Figure 16:
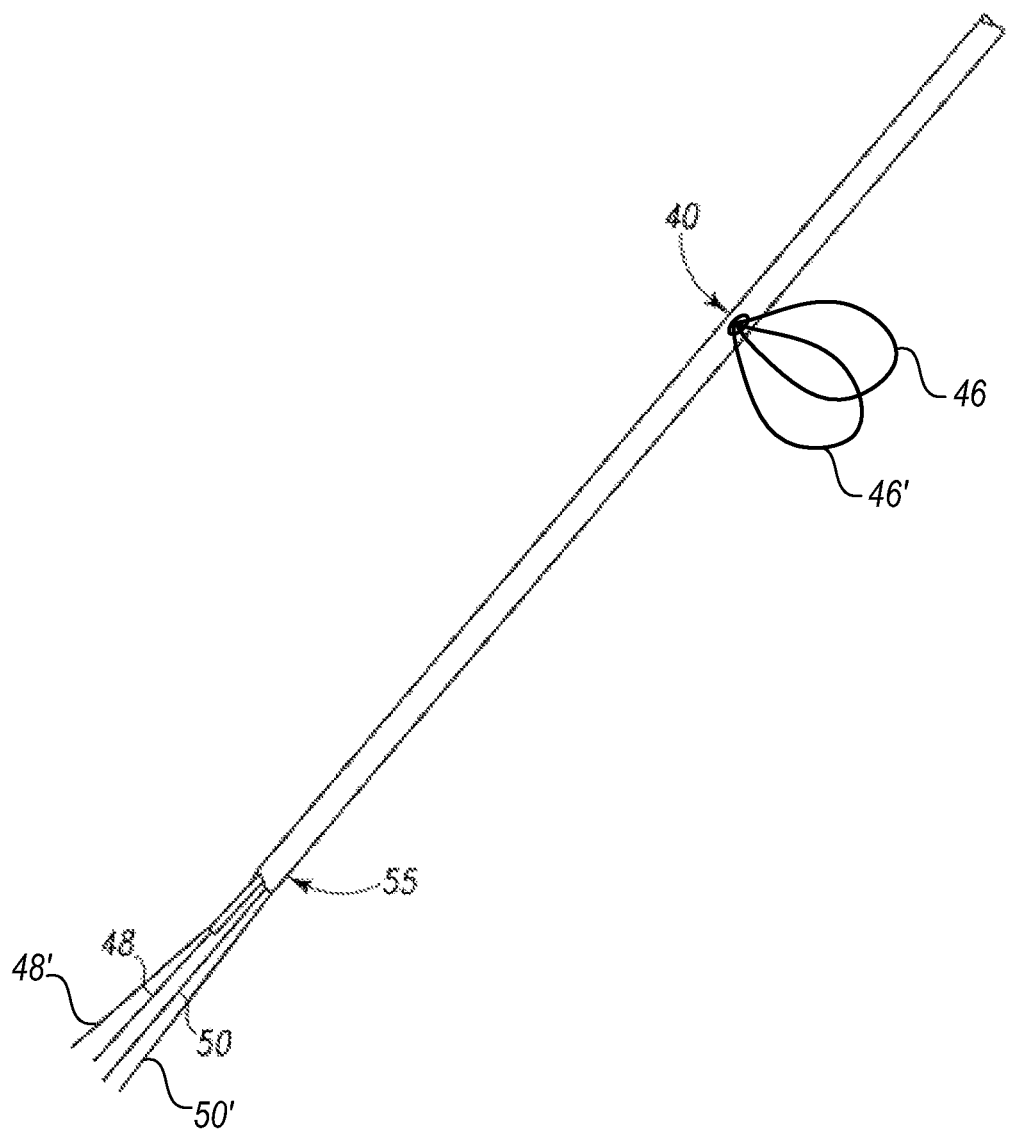
FIG. 16 is a perspective partial view of the snare catheter with the snare mechanism extending from the opening system and formed of two wires.
Figure 17:
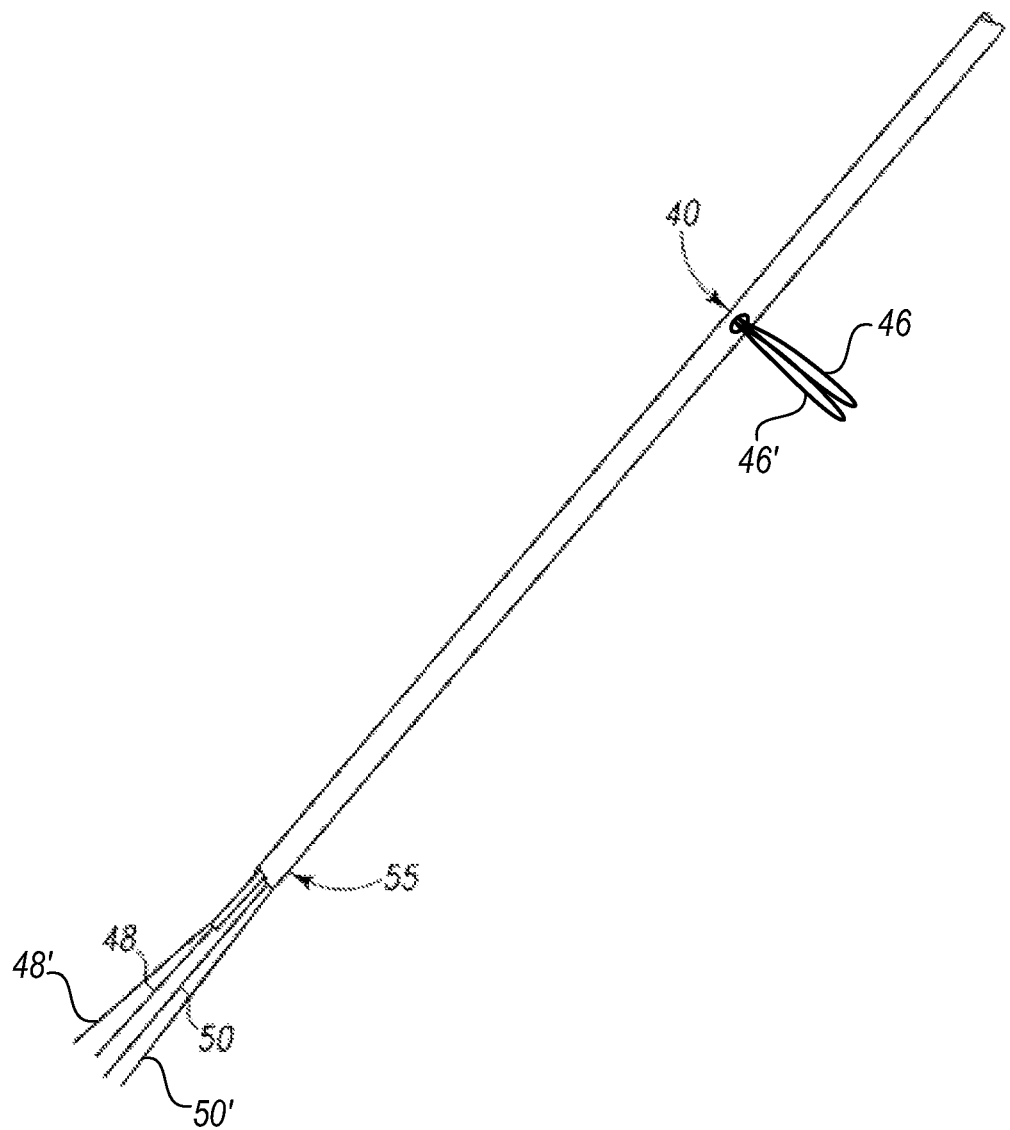
FIG. 17 is another perspective partial view of the snare catheter with the snare mechanism extending from the opening system and formed of two wires.

FIG. 9 is a partial perspective view of the snare catheter 40 having a two hole system where the holes 54, 56 are approximately 180 degrees spaced apart and the snare mechanism has been advanced out of the catheter The snare mechanism may be a single wire 48, 50, or as shown in FIGS. 16 and 17, multiple wires 48, 48', 50, 50' or a cable formed of two or more wires. Where one wire is used, the wire may be provided with sections of radiopacity for imaging during the procedure. The snare mechanism also may comprise two or more wires 48, 48', 50, 50'. The wires may be twisted or braided to form a cable. In addition, the multiple wires may be formed of different materials, for example, in a twisted cable of multiple wires, one or more wires may comprise a material that is more radiopaque than the other wires so as to impart visibility to the snare during the procedure. In one example, the snare is one or more wires formed of a shape memory alloy, such as Nitinol. In another example, the snare mechanism material is a linear elastic material. The snare material also may be formed of other metal, alloy plastic, polymeric, or other suitable material or combination of materials.

As previously discussed, the snare catheter 40 is preloaded with the main body prosthesis 10 into the main body delivery device 20. In the delivery device 20, a portion of the snare catheter 40 is disposed externally to and along side the prosthetic device (not shown). For example, a portion of the snare catheter 40 is disposed along side the external surface of the ipsilateral limb 14. Another part of the snare catheter 40, preferably above the opening system 44, is disposed within at least the contralateral limb 16 and possibly up into the lumen of the main body 12.

Figure 10:
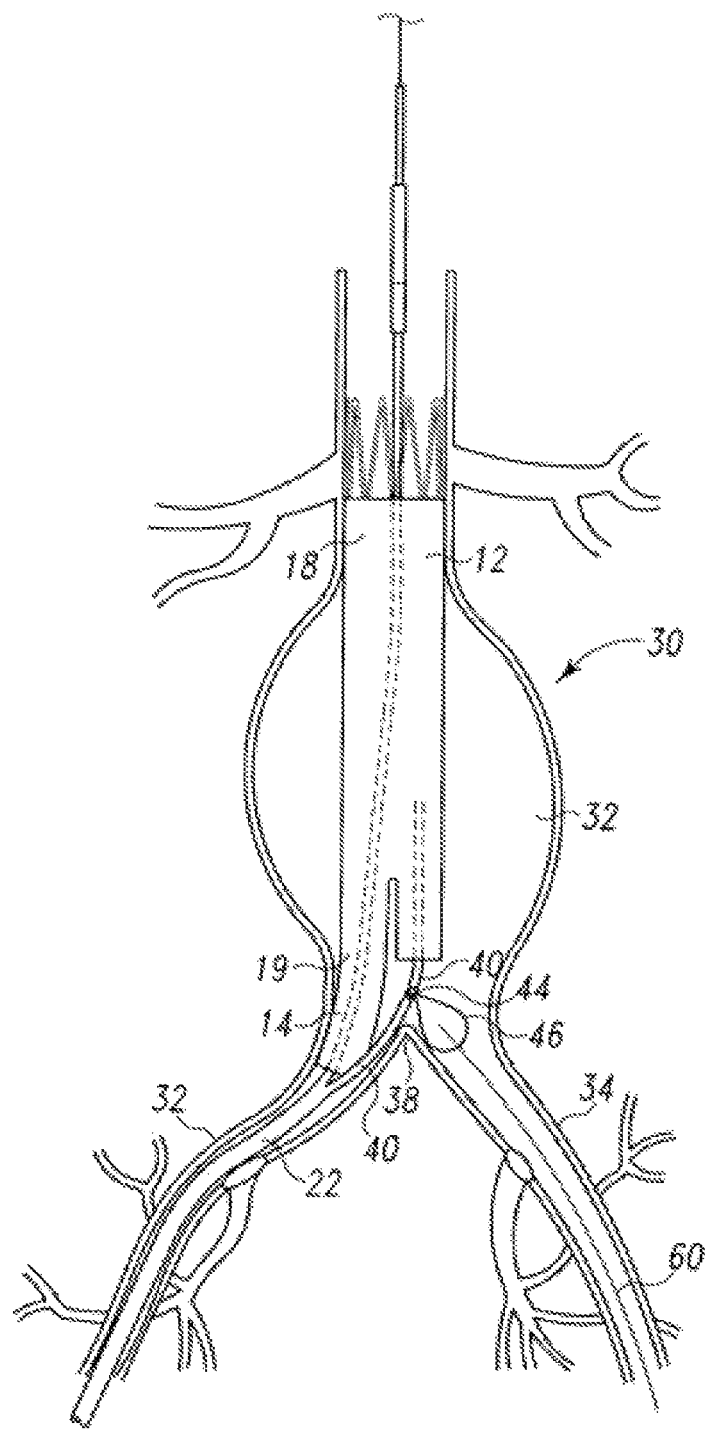
FIG. 10 shows a deployed prosthesis and a snare catheter extending into a contralateral limb of the deployed device.

Using imaging techniques, such as fluoroscopy, the main delivery device 20, including the prosthesis 10 to be placed and the snare catheter 40, all enclosed by sheath 22, is advanced through an incision in one of the femoral arteries to the target delivery site of the prosthesis. As shown in FIG. 10, once the main body 12 has been placed at the target location, a guidewire 60 is advanced through the other femoral artery, through the contralateral iliac artery 34 and into the aorta at a point below the opening of the contralateral limb 16.

As shown in FIG. 10, the snare catheter 40, having been released at least partially from the sheath 22 by way of withdrawing the sheath or advancing the snare catheter 40, is moved to a location within the body vessel in the vicinity of the guidewire 60. The snare mechanism 42 is advanced out of the hole (embodiment) or advanced out of one or both holes (in the two hole embodiment) to form a loop 46 external to the snare catheter 40.

Figure 11:
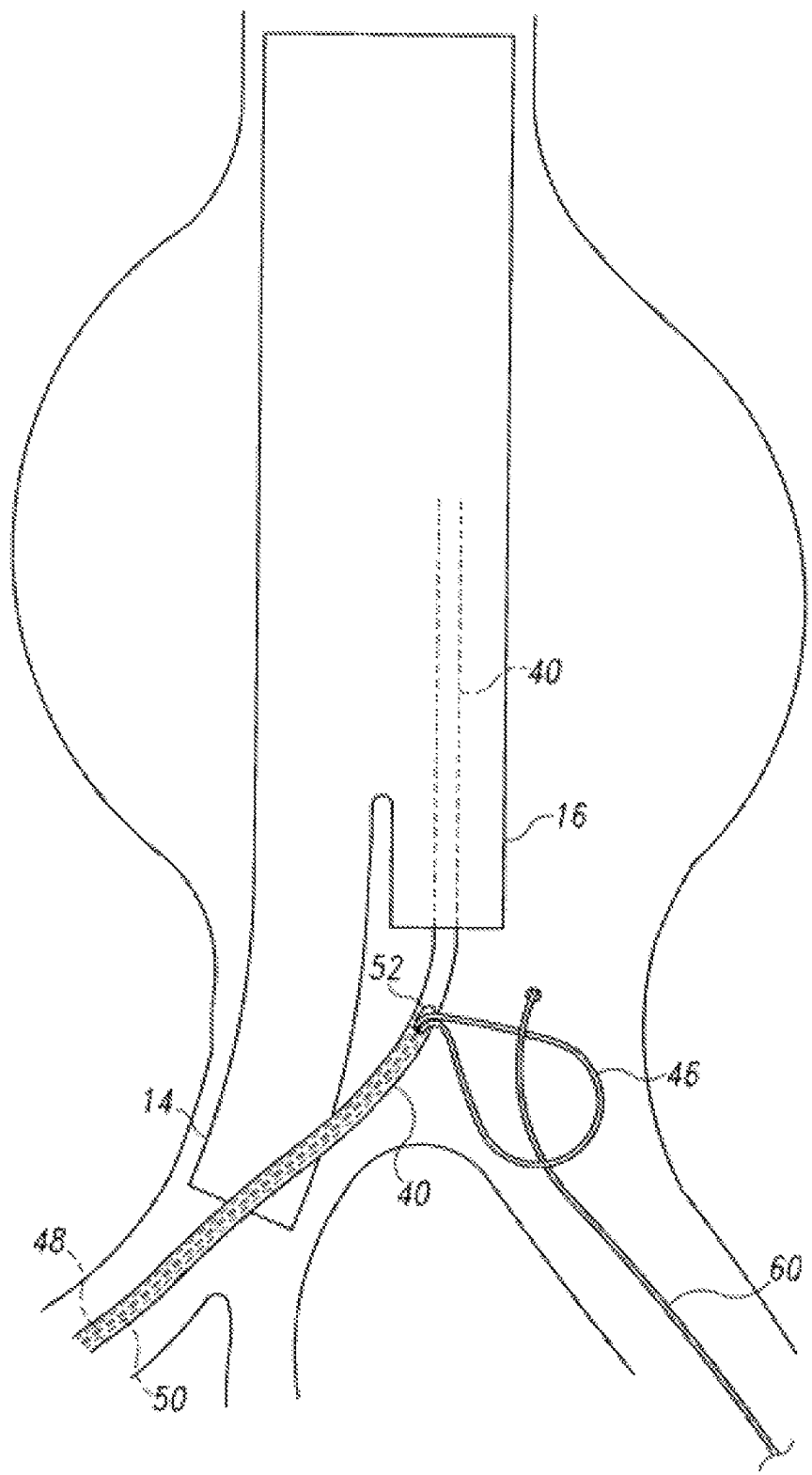
FIG. 11 shows the snare mechanism engaging a guidewire.
Figure 12:
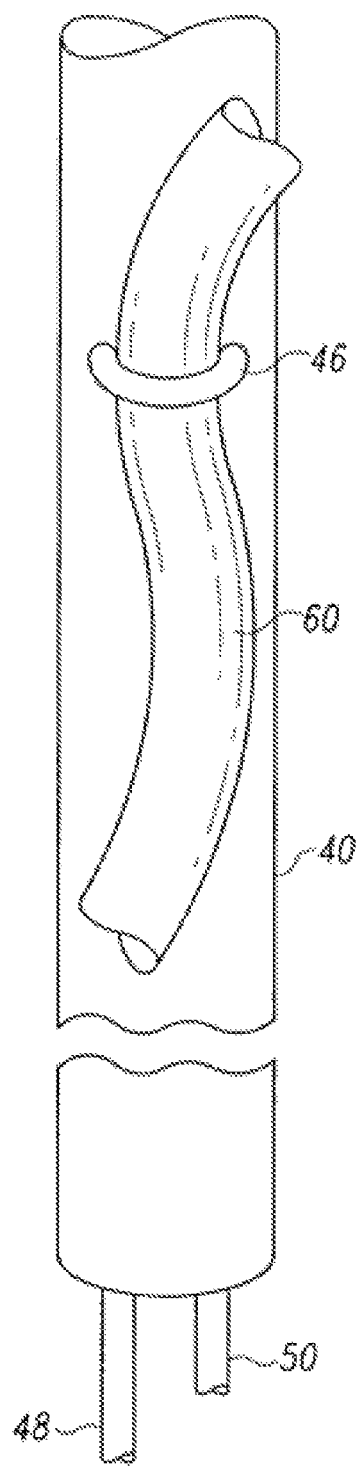
FIG. 12 is a partial view of the snare catheter having engaged the guidewire pulled it taut to the surface of the snare catheter.

As shown in FIG. 11, the loop 46 catches the guidewire 60 within the loop 46. As shown in FIG. 12, the physician or other technician withdraws or retracts the snare mechanism to manipulate the snare loop to pull the guidewire toward the snare catheter 40 to generally secure the guidewire 60 against the outside of the snare catheter 40.

Figure 13:
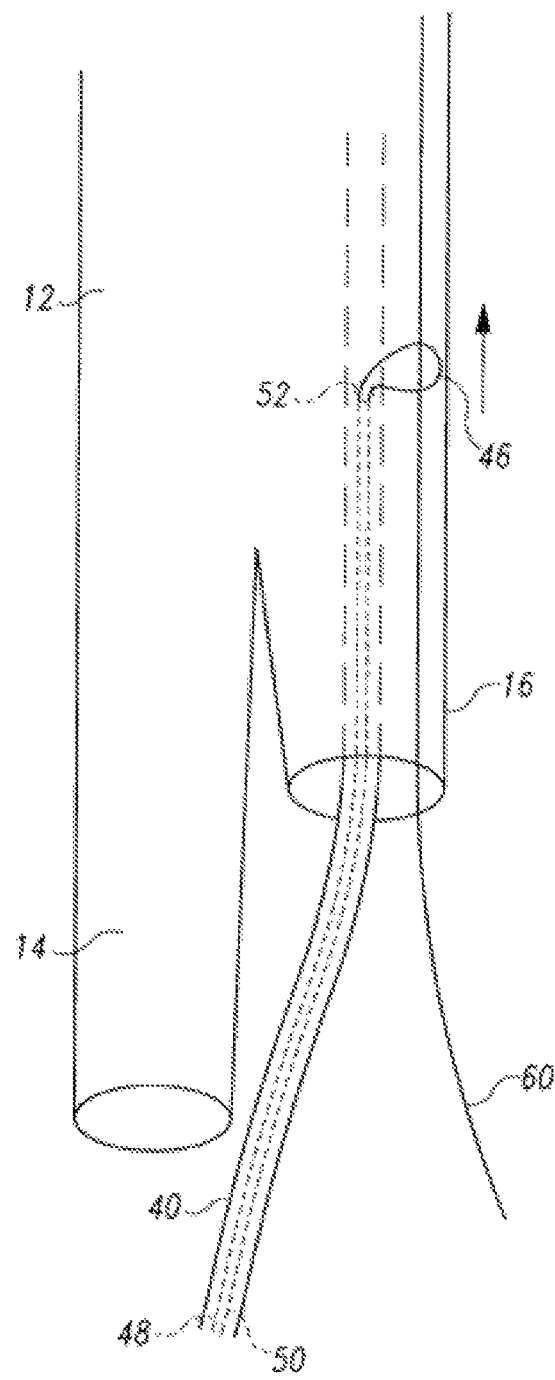
FIG. 13 shows the advancement of the snare catheter with the engaged guidewire advancing into the lumen of the prosthesis.
Figure 14:
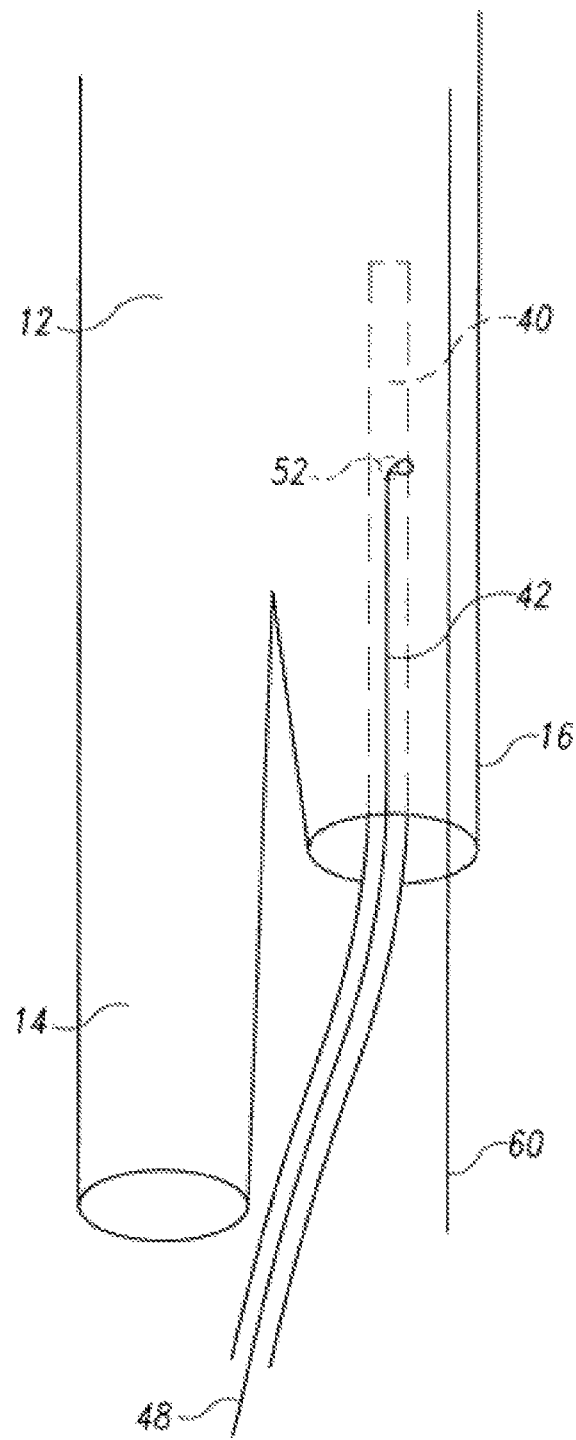
FIG. 14 shows the snare mechanism releasing the guidewire.

The snare catheter 40, with the ensnared guidewire 60, may then be advanced further (as shown by the arrow in FIG. 13) into the contralateral limb 16, and the body 12 of the prosthesis, at which point the guidewire 60 may be released from the snare loop 46. The guidewire 60 may be released from the snare loop 46 by lifting the loop off of the end of the snare, or pulling one end of the snare mechanism until the other end pulls through the loop 46 and back through the opening system, as shown in FIG. 14. Preferably, the snare catheter 40 is advanced into the main body 12 of the prosthesis so that when the guidewire 60 is released, a portion of the guidewire 60 resides in the main body 12 lumen, as shown in FIG. 14.

Figure 15:
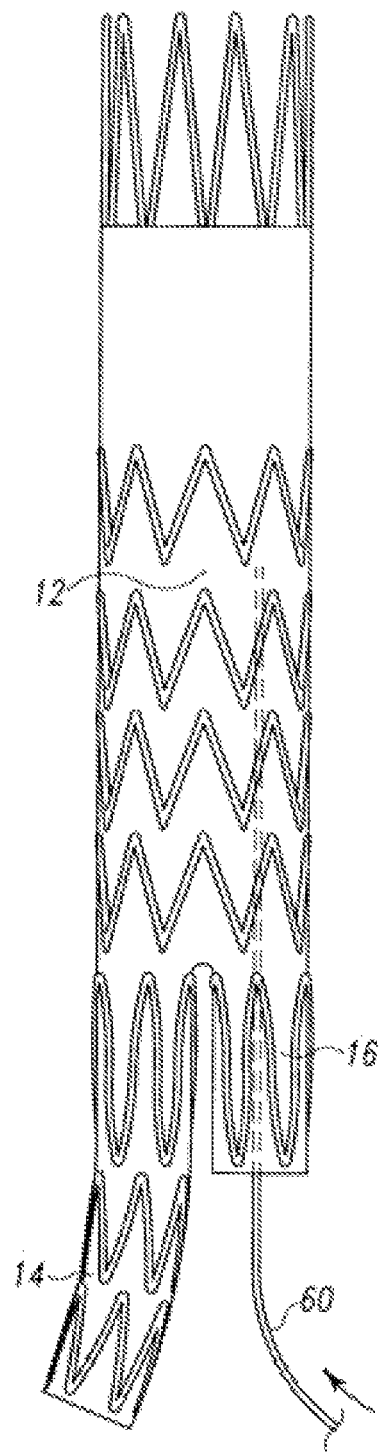
FIG. 15 shows the prosthesis after the snare mechanism has been removed leaving the guidewire in place in the contralateral limb and the lumen of the prosthesis.

The guidewire catheter may then be removed from the patient's body. Thereafter, a second delivery system carrying a contralateral leg extension (not shown) may be advanced over guidewire 60 and docked with the contralateral limb 16 in the direction shown by the arrow in FIG. 15.

The materials used in the manufacture of the stent for the prosthesis described here may be selected from a well-known list of suitable metals. Preferred materials include those materials that can provide the desired functional characteristics with respect to mechanical load bearing, biological compatibility, modulus of elasticity or other desired properties. In various embodiments, the stent includes a metallic material selected from stainless steel, nickel, silver, platinum, palladium, gold, titanium, tantalum, iridium, tungsten, cobalt, chromium, a nickel-titanium alloy, a superelastic nickel-titanium (NiTi) alloy sold under the tradename NITINOL® or inconel.

The stent may be attached to graft material to form the endoluminal device. The graft material may be attached to the stent by any appropriate attachment means, including but not limited to stitching using sutures, adhesive, fasteners, and tissue welding using heat and/or pressure. Suture material may be polypropylene or any other suitable material known in the art.

The graft material may be constructed from a biocompatible textile fabric, a polymer, biomaterial, or a composite thereof. Examples of biocompatible materials from which textile graft material can be formed include polyesters, such as polyethylene terephthalate); fluorinated polymers, such as polytetrafluoroethylene (PTFE) and fibers of expanded PTFE; and polyurethanes. Preferably, the graft material is a woven polyester. More preferably, the graft material is a polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids. The woven polyester of the graft material may comprise a plurality of yarns.

It is therefore intended that the foregoing detailed description be regarded as illustrative rather than limiting, and that it be understood that it is the following claims, including all equivalents, that are intended to define the scope of this invention.

The invention claimed is:

1. An endovascular delivery system comprising:
a delivery device for delivering a prosthesis to a body vessel, the delivery device comprising a sheath;
a bifurcated prosthesis disposed in the sheath of the delivery device and having a main body, a first limb and a second limb, each limb having a lumen;
a snare catheter, pre-loaded with the bifurcated prosthesis in the sheath, and having a proximal end, a distal end, a lumen therebetween, and a snare opening system between the proximal end and the distal end;
a snare mechanism disposed within the snare catheter that is capable of forming a loop external to the snare catheter and having at least one free end exiting the snare catheter distal end;
where at least a portion of the snare catheter is positioned external to and adjacent to the bifurcated prosthesis and at least a portion of the snare catheter is positioned within the lumen of one of the limbs, and both portions are enclosed within the sheath.

2. The delivery system of claim 1 where the snare catheter further comprises a snare stopping mechanism within the snare catheter and proximally adjacent the snare opening system.

3. The delivery system of claim 1 where the snare opening system comprises at least one hole.

4. The delivery system of claim 3 where the snare opening system comprises two holes.

5. The delivery system of claim 1 where the snare mechanism comprises at least one wire.

6. The delivery system of claim 5 where the snare mechanism comprises a plurality of wires, where at least one of the plurality of wires is imagable.

7. The delivery system of claim 1 where the first limb is longer than the second limb.

8. The delivery system of claim 7 where the portion of the snare catheter positioned external to the bifurcated prosthesis is adjacent the longer limb and a portion of the snare catheter proximal to the opening system is positioned within the shorter second limb.

9. The delivery device of claim 1 comprising at least two or more of any of the following: a snare stopping mechanism within the snare catheter and proximally adjacent the snare opening system; the snare opening system comprising at least one hole; the snare opening system comprising at least two holes; the snare mechanism comprising at least one wire; the snare mechanism comprising a plurality of wires, where at least one of the plurality of wires is imagable; and a first limb that is longer than the second limb and where the portion of the snare catheter positioned external to the prosthesis is adjacent the longer limb and a portion of the snare catheter proximal to the snare opening system is positioned within the shorter second limb.

10. The endovascular delivery system of claim 1, wherein the sheath is a retractable sheath slidably disposed over the bifurcated prosthesis and at least a portion of the snare catheter including the snare opening system.

11. An endovascular delivery system for delivering a bifurcated prosthesis to a body vessel having a bifurcation comprising:
a delivery device having a sheath; a bifurcated prosthesis disposed within the sheath of the delivery device and having a main body, a first limb and a second limb, the body and each limb having a lumen in fluid communication with each other, where the bifurcated prosthesis is configured to be positioned in the body vessel and where, when the prosthesis is so positioned, at least one limb is above the bifurcation of the body vessel;
a snare catheter preloaded with the bifurcated prosthesis in the sheath, and having a proximal end, a distal end, a lumen therebetween, and a snare opening system between the proximal end and the distal end; a snare mechanism disposed within the snare catheter that is capable of forming a loop external to the snare catheter and having at least one free end exiting the snare catheter distal end;
where at least a portion of the snare catheter is positioned external to and adjacent to one limb of the prosthesis and at least a portion of the snare catheter proximal to the snare opening system is positioned within the lumen of the other limb, and wherein both portions are enclosed within the sheath.

12. The delivery system of claim 11 where the snare catheter further comprises a snare stopping mechanism within the snare catheter that is disposed proximal of and adjacent to the snare opening system.

13. The delivery system of claim 11 where the snare opening system comprises at least one hole.

14. The delivery system of claim 13 where the snare opening system comprises two holes.

15. The delivery system of claim 11 where the snare mechanism comprises at least one wire.

16. The delivery system of claim 15 where the snare mechanism comprises a plurality of wires where at least one of the plurality of wires is imagable.

17. The delivery system of claim 11 where the first limb is longer than the second limb.

18. The delivery system of claim 17 where the portion of the snare catheter positioned external to the bifurcated prosthesis is adjacent the longer limb and a portion of the snare catheter proximal to the opening system is positioned within the shorter second limb.

19. The endovascular delivery system of claim 11, wherein the sheath is a retractable sheath slidably disposed over the bifurcated prosthesis and at least a portion of the snare catheter including the snare opening system, wherein the snare mechanism is capable of forming a loop external to the snare catheter upon retraction of the sheath.

20. A method of cannulating a limb of a bifurcated device having a first limb and a second limb shorter than the first limb comprising: providing a delivery device for delivering the prosthesis to a body vessel, the delivery device including a sheath, and the method comprising: a bifurcated prosthesis disposed within the sheath of the delivery device; a snare catheter preloaded with the bifurcated prosthesis within the sheath and having a portion that is partially adjacent the bifurcated prosthesis and portion residing within the second limb in a predeployment state and having a snare opening system and a snare mechanism, all of which are enclosed with the prosthesis within the sheath; introducing the delivery device into a first artery of a patient and delivering the delivery device to a site for implantation of the bifurcated prosthesis; at least partially expanding the prosthesis at the delivery; introducing a guidewire into a second artery and directing the guidewire to an area below the second limb; thereafter maneuvering the snare mechanism out of the snare opening system to form a loop external to the snare opening system; maneuvering the loop to ensnare the guidewire within the loop; retracting the loop toward the snare catheter to secure the guidewire to the snare catheter; advancing the snare catheter further into the bifurcated prosthesis such that the snare opening system resides at least within a lumen of the bifurcated prosthesis; releasing the guidewire from the snare loop; and retracting the snare catheter from the bifurcated prosthesis.

21. The method of claim 20 where the snare mechanism has two ends within the catheter where the step of releasing the guidewire comprises retracting one of the ends of the snare mechanism by pulling on the end until the other end of the snare mechanism travels proximally through the snare catheter, exits the snare opening system and at least partially reenters the snare opening system.

22. The method of claim 20, wherein the sheath is a retractable sheath slidably disposed over the bifurcated prosthesis and at least a portion of the snare catheter including the snare opening system, and further comprising the step of removing the sheath from the prosthesis to at least partially deploy the prosthesis at the delivery site and uncover at least a portion of the snare catheter including the snare opening system.

23. A prosthesis cannulation system comprising: a delivery catheter having a sheath; a bifurcated prosthesis disposed in the sheath of the delivery catheter; a snare catheter preloaded with the bifurcated prosthesis within the sheath and disposed at least adjacent the delivery catheter and having a snare opening system and a snare mechanism disposed within the snare catheter; wherein the snare catheter has a portion that resides outside the bifurcated prosthesis and a portion that resides within the bifurcated prosthesis in a predeployment state, wherein both portions are enclosed within the sheath in the predeployment state.

24. The prosthesis cannulation system of claim 23, wherein the sheath is a retractable sheath slidably disposed over the bifurcated prosthesis and at least a portion of the snare catheter including the snare opening system.

* * * * *